(12) United States Patent
Dorsey et al.

(10) Patent No.: US 8,790,657 B2
(45) Date of Patent: Jul. 29, 2014

(54) ASTROVIRUS

(75) Inventors: Kristi Mae Dorsey, Shawnee, KS (US); John Knox Rosenberger, Lincoln University, PA (US); Sandra Cloud Rosenberger, Lincoln University, PA (US)

(73) Assignee: Biomune Company, Lenexa, KS (US)

( * ) Notice: Subject to any disclaimer, the term of this patent is extended or adjusted under 35 U.S.C. 154(b) by 536 days.

(21) Appl. No.: 13/000,477

(22) PCT Filed: Jun. 26, 2009

(86) PCT No.: PCT/US2009/048854
§ 371 (c)(1),
(2), (4) Date: Jan. 11, 2011

(87) PCT Pub. No.: WO2009/158614
PCT Pub. Date: Dec. 30, 2009

(65) Prior Publication Data
US 2011/0171253 A1    Jul. 14, 2011

Related U.S. Application Data

(60) Provisional application No. 61/076,058, filed on Jun. 26, 2008.

(51) Int. Cl.
*A61K 39/12* (2006.01)
*A01N 63/00* (2006.01)
*A61K 39/295* (2006.01)
*C12N 7/00* (2006.01)

(52) U.S. Cl.
USPC .................. 424/204.1; 424/186.1; 424/202.1; 424/93.6; 424/93.7; 435/235.1

(58) Field of Classification Search
None
See application file for complete search history.

(56) References Cited

U.S. PATENT DOCUMENTS

2005/0079485 A1    4/2005  Schultz-Cherry et al.

FOREIGN PATENT DOCUMENTS

WO    WO 2004/027053 A    4/2004

OTHER PUBLICATIONS

Goodwin et al, "A high-throughput, high-resolution strategy for the study of site-selective DNA binding agents: analysis of a "highly twisted" benzimidazole-diamidine," J Am Chem Soc 128(24): pp. 7846-7854 (2006).*
From NCBI Blast, "Chain G, D (Cttgaatgcattcaag) in Complex With Mmlv Rt Catalytic Fragment" from Goodwin et al. (2006).*
De Benedictis et al., "Astrovirus infections in humans and animals—Molecular biology, genetic diversity, and interspecies transmissions," Infection Genetics and Evolution 11, pp. 1529-1544 (2011).*
Baxendale, et al., "The Isolation and Characterization of Astroviruses from Chickens", Avian Pathology, vol. 33(3):364-370, (2004).

(Continued)

*Primary Examiner* — Michelle S Horning
*Assistant Examiner* — M. Franco Salvoza
(74) *Attorney, Agent, or Firm* — Saliwanchik, Lloyd & Eisenschenk (57) ABSTRACT

This invention relates to the isolation and uses of novel avian astroviruses. The present invention also relates to vaccines, kits and methods for detection of a novel astrovirus. The present invention further relates to vaccination of avians, prevention and/or treatment of avian infections associated with astrovirus. Infections of poultry by this novel astrovirus are associated with runt stunting syndromes.

16 Claims, 8 Drawing Sheets

SEQUENCE ID NO: 1

TGGTGGTGCTTCCTTAAAAATGAAGTTCTCAAGAAAAAGAAAATTCAAGAGAATGATATTAGAATGATCTTATGTACTGATCCAGTTTTTACC
CGAATTGGCGCAATGTTTGATCAGGATCAGAATTCAAAAATGAAAAATATGACAGAGACGAGAGCTGCACAGGTGGGCTGGACCCCATTT
TTTGGTGGACTTGACCAACGAGTGCGGAGATTGGAGAAGATAAAGAACGCCCAGTTTGTAGAGATGGATTGGACCCGTTTTGATGGCACT
ATTCCAAAAGCACTCTTCTGGCGTATCCGGCAAATCAGATTCTTTCTCCTGGCGCCCCGGTATAAAACCGAGGAAAATAAGGAGTTGTTTGA
TTGGTATACAAAGAATCTGCTGGAGAAAATTATCTTGTTACCAACCGGAGAGGTGTGCCAAGTCAAAAGAGGGAATCCTTCTGGGCAATTC
TCCACAACAGTTGACAACAATATGTGCAATGTGTGGTTAACTACCTTTGAAATTGCATGGCTCCACCGCAAGCAAAAAGGTAGATTGCCCAC
TCCCATTGAGTTGAATAAAAATCTTAGATACATTTGTTACGGTGATGACAGGCTCTTGGCAGTCTCTAAAGACCTTGTTACCTATGAGCCTGA
TTCTGTAGTTGAAATGTATGCAGATGTCTTTGGGATGTGGGTCAAACC (56) References Cited

OTHER PUBLICATIONS

Pantin-Jackwood et al., 2006, "Molecular Characterization and Typing of Chicken and Turkey Astroviruses Circulating in the United States: Implications for Diagnostics", Avian Diseases, vol. 50(3): 397-404.

PCT International Search Report, Nov. 12, 2009 for Int'l App'l No. PCT/US2009/048854, filed Jun. 26, 2009.

PCT Written Opinion of the International Searching Authority, Nov. 12, 2009, for Int'l App'l No. PCT/US2009/046854, filed Jun. 26, 2009.

\* cited by examiner

FIGURE 1

SEQUENCE ID NO: 1

TGGTGGTGCTTCCTAAAAATGAAGTTCTCAAGAAAAAGAAAATTCAAGAGAATGATCTTATGTACTGATCCAGTTTTACC
CGAATTGGGCGCCAATGTTTGATCAGGATCAGAGATCAGATAATGACAGAGACGAGAGCTGCACAGGTGGGCTGGACCCATT
TTTGGTGGACTTGACCAACGAGTGCGGAGATTGGGAGAAGATAAAGAACGCCCAGTTTGTAGAGATGGATTGGACCCGTTTGATGGCACT
ATTCCAAAAGCACTCTTCTGGCGTATCCGGCAAATCAGATTCTTCCTGGCCGTATAAAACCGAGGAAAATAAGGAGTGTTTGA
TTGGTATACAAAGAATCTGCTGGAGAAATTATCTTGTTACCAACCGGAGAGGGTGTGCCAAGTCAAAAGAGGAATCCTTCTGGGCAATTC
TCCACACAGTTGACAACAATATGTGCAATGTGTGGTTAACTACCTTTGAAATTGCATGGTCTCCACCGCAAGCAAAAGGTAGATTGCCCAC
TCCCATTGAGTTGAATAAAAATCTTAGATACATTTGTTACGGTGATGACAGGCTCTTGGCAGTCTCTAAAGACCTTGTTACCTATGAGCCTGA
TTCTGTAGTTGAAATGTATGCAGATGTCTTTGGGATGTGGGTCAAACC

ASTROVIRUS

This application is the National Stage of Int'l App'l No. PCT/US2009/048854, filed Jun. 26, 2009, which claims priority of U.S. Ser. No. 61/076,058, filed Jun. 26, 2008. The entire contents and disclosures of the preceding applications are incorporated by reference into this application.

Throughout this application, various references or publications are cited. Disclosures of these references or publications in their entireties are hereby incorporated by reference into this application in order to more fully describe the state of the art to which this invention pertains.

FIELD OF THE INVENTION

This invention relates to the isolation and uses of novel avian astroviruses. The present invention also relates to vaccines, kits and methods for detection of a novel astrovirus. The present invention further relates to vaccination of avians, prevention and/or treatment of avian infections associated with astrovirus. Infections of poultry by this novel astrovirus are associated with runt stunting syndromes.

BACKGROUND OF THE INVENTION

Astrovirus

Astroviruses were first identified in 1980 by McNulty et al. from the intestinal contents of 11-day-old turkey poults with diarrhea and increased mortality. Subsequently, astroviruses in flocks of young turkeys were reported in the United States in 1985, 1986, and most recently in 2000.

Astroviruses cause, or have been associated with, acute gastroenteritis in humans, cattle, swine, sheep, cats, dogs, deer, mice, and turkeys, as well as fatal hepatitis in ducks. In chickens, avian nephritis virus (ANV) was reclassified as an Astroviridae based on genomic organization. More recently, astroviruses have been detected in birds with poult enteritis and mortality syndrome (PEMS). Astroviruses are seldom the only virus detected in flocks with enteric disease. Generally, they occur with other enteric viruses, especially group D rotavirus.

Astroviruses are small, round viruses typically 25-35 nm in diameter. They get their name from the 5 or 6 pointed star-like surface projections observed using electron microscopy. However, only 10% of astroviruses in a population may exhibit this morphology, and visualization is dependent on sample preparation. Astroviruses are nonenveloped, positive sense RNA viruses. Their viral genome is 6.5-7.5 kilobases long and contains 3 open reading frames (ORF). These reading frames code for nonstructural proteins (ORF1a), a viral RNA dependant-RNA polymerase (ORF1b), and precursor capsid protein (ORF2).

Astroviruses are distinct molecularly from picornaviruses in that they synthesize a subgenomic message during replication and differ from picornaviruses and caliciviruses in that they have a retrovirus-like frame shift signal sequence between ORF1a and ORF1b. Currently, only the human astrovirus (HAstV), 2 distinct strains of turkey astrovirus (TAstV), swine astrovirus (SAstV), and avian nephritis virus (ANV) have had their genomes fully sequenced. The avian astroviruses are molecularly distinct, sharing very little sequence similarity in the different gene segments. However, the turkey astroviruses cluster into a distinct group from ANV.

Avian Nephritis Viral Infections

Avian nephritis viral infections are contagious infections of chickens and turkeys characterized by renal damage and visceral urate deposits, growth retardation, runting and stunting syndrome, and limited mortality (2-6%). They are seen mainly in chickens<7 days old, but interstitial nephritis can be observed in chicks up to 4 week old. These infections have been reported worldwide. Subclinical infections are common and have been detected by serologic surveys in some SPF flocks. The causal viruses are avian nephritis virus (ANV, an astrovirus), ANV-like viruses, and related enterovirus-like viruses (ELV). Strains vary in virulence and in antigenicity. Transmission occurs by direct or indirect contact. Indirect evidence suggests that egg transmission may occur. Infection can be transmitted by oral administration of virus to day-old birds. Virus is consistently isolated from the kidneys or the feces during the first 10 days after infection. Clinical signs vary from none to the so-called Runting and Stunting Syndrome (RSS). Diarrhea and growth retardation are common in broilers. Outbreaks with mortality of 2-6% can occur in chicks newly hatched up to 7 days old; cardinal necropsy findings are renal damage and visceral urate deposits (baby chick nephropathy).

Avian Malabsorption Syndrome

Avian Malabsorption Syndrome (MAS) is a disease of growing poultry, especially chickens, with meat-type or broilers being affected most commonly. This disease has been reported in the Netherlands (Kouwenhoven et al., 1978) as Runting and Stunting Syndrome (RSS) but also under different names worldwide as for example infectious stunting syndrome, enteritis, pale bird syndrome, helicopter disease, infectious proventriculitis, brittle bone disease and femoral head necrosis.

Kouwenhoven et al. (Avian Pathology 17:879-892, (1988)) further defined MAS by five criteria: 1) growth impairment up to 3 weeks after infection of one-day old chicks; 2) excretion of yellow orange mucoid to wet droppings; 3) increased plasma alkaline phosphatase (ALP) activity; 4) decreased plasma carotenoid concentration (PCC); and 5) macroscopically widened epiphyseal growth plates of the proximal tibia. The condition has been further characterized by stunted growth, poor feathering, maldigested feed, lack of skin pigmentation, enteritis, pancreatic atrophy, proventriculitis, thymic and bursal atropy and bone changes.

Vertommen et al. (1980) describe the transmission of the disease by oral inoculation of intestinal homogenates from affected chicks into one-day-old broilers. In that experiment, it was demonstrated that low plasma carotenoid levels and elevated ALP activities are suitable tools for the diagnosis of MAS. In further experiments, MAS was transmitted by oral inoculation of liver homogenates from affected chicks into one-day-old broilers. Despite years of research, the etiology of MAS has not yet been fully established, and the condition is still a major problem for the poultry industry. It is believed that a virus is responsible, but bacteria or other microorganisms have not been excluded as causal agents.

Viruses that have been associated with outbreaks of MAS and/or of nephritis possibly include astroviruses, rotaviruses, parvoviruses, entero-like viruses and a toga-like virus (McNulty and McFerran, 1993). McNulty (World Poultry 14:57-58 (1998)), summarized the state of art on MAS, and has postulated that identification of the causative agent is still unknown and recommends control by careful management of production sites.

SUMMARY OF THE INVENTION

The present invention provides a novel isolated astrovirus serotype, designated AVS-1, which has been deposited with the American Type Culture Collection ("ATCC" 10801 University Boulevard, Manassas, Va. 20110-2209 USA) under Budapest Treaty on Jun. 26, 2008, and has accession number PTA-9298. The novel astrovirus serotype has been characterized herein as possible viral agent causing avian infections.

In another embodiment, there is provided a vaccine for use in the protection and a method of vaccination of poultry against disease conditions resulting from an avian astrovirus infection, comprising the astroviruses disclosed herein, and a pharmaceutical acceptable carrier.

The present invention also provides antiserum that is induced in an animal by the astroviruses disclosed herein. In another embodiment, there is also provided antibodies that bind to the astroviruses disclosed herein.

The present invention also provides a method of protecting poultry against disease conditions resulting from an avian astrovirus infection, comprising the step of administering the vaccine disclosed herein to the poultry.

In particular, poultry disease conditions include MAS or Runt Stunting syndrome.

A region of the genome of the AVS-1 has been sequenced. This region comprises a nucleotide sequence as set forth in SEQ ID NO: 1, or a nucleotide sequence which has at least 85%, preferably at least 90%, 93%, more preferably 95% or 98%, or between 98 and 100% sequence identity to the sequence as set forth in SEQ ID NO: 1, or with a fragment thereof. It is also provided a nucleotide sequence capable of hybridizing to SEQ ID NO: 1 under stringent conditions and fragments thereof.

The present invention also provides a method of detecting the presence of avian astrovirus in poultry, comprising the steps of: obtaining a sample from the poultry; contacting the sample with antibodies that bind to the astroviruses disclosed herein; and detecting binding of the antibodies to the sample, wherein detected binding would indicate the presence of astroviruses of the present invention in the poultry.

BRIEF DESCRIPTION OF THE FIGURES

FIG. 2(A-E): shows amino acid alignment of the nucleotide sequence of AVS-1 as set for the in SEQ ID NO: 1 (designated ASTHB) with same region of astroviruses isolated from similar clinical cases (designated ASTV (SEQ ID NO: 4), ASTLE (SEQ ID NO: 5), ASTPL (SEQ ID NO: 6), ASTEK (SEQ ID NO: 7)). Using the ClustalW multiple sequence alignment program, the nucleotide sequence alignment revealed 99.3-99.7% similarity to the AVS-1 isolate.

DETAILED DESCRIPTION OF THE INVENTION

In one embodiment, the present invention provides a new antigenic class of avian astroviruses. In particular, the present invention provides a novel isolated astrovirus serotype designated AVS-1 which has been deposited with the American Type Culture Collection ("ATCC" University Boulevard, Manassas, Va. 20110-2209 USA) under Budapest Treaty on Jun. 26, 2008, and has accession number PTA-9298. Newly characterized astrovirus AVS-1 is antigenically distinct from previously known astrovirus.

Also, a portion of the genome of the AVS-1 isolate has been sequenced. The sequence comprises part of the polymerase gene from the new astrovirus isolate AVS-1. Comparison of the sequence with other well known astroviruses show sequence similarity between 73-75% to other well known astroviruses, and 91% similar to sequences on Genbank, thereby clearly showing that the novel serotype distinct from previously known strains has been isolated.

The present invention thus provides an isolated nucleotide sequence which has at least 85%, preferably at least 90%, 93%, more preferably 95% or 98%, or between 98 and 100% sequence identity to the sequence as set forth in SEQ ID NO: 1, or with a fragment thereof. It is also provided a nucleotide sequence capable of hybridizing to SEQ ID NO: 1 under stringent conditions and fragments thereof.

Sequence identity or identity percentage refers to a specified percentage of residues in the two sequences that are the same when aligned for maximum correspondence over a specified comparison window, as measured by sequence comparison algorithms or by visual inspection. This is determined In relation to nucleotide sequences provided by the invention, sequence identity is determined using a suitable mathematical algorithm. Computer implementations of such mathematical algorithms can be utilized for comparison of sequences to determine sequence identity. Such implementations include, but are not limited to: CLUSTAL in the PC/Gene program; the ALIGN program and BESTFIT, BLAST, FASTA.

Hybridization refers to the binding or formation of duplex, or hybridizing of a molecule only to a particular nucleotide sequence under stringent conditions when that sequence is present in a poultry sample DNA or RNA. Typically, to achieve stringent hybridization, temperatures of around 5° C. to about 20° C. below the Tm (melting temperature at which half the molecules dissociate from their partner) are used. Such conditions are further defined by ionic strength and pH of the solution. For example, highly stringent hybridization conditions are achieved at 0.15 M NaCl at 72° C. for about 15 minutes. An example of a stringent wash condition is a 0.2× SSC wash at 65 C for 15 minutes. An example of a medium stringency wash for DNA duplex of, for example, more than 100 nucleotides, is 1×SSC at 45 C for 15 minutes. An example of a low stringency wash for a duplex of for example more than 100 nucleotides is 4-6×SSC at 40° C. for 15 minutes. For short probes of 10 to 50 nucleotides, stringent conditions typically involve salt concentrations of less than about 1.5 M, more preferably about 0.01 to 1.0 M, Na ion concentration at pH 7.0 to 8.3, and the temperature is typically at least about 30° C. and at least about 60° C. for long probes of about 50 nucleotides.

The present invention also provides amino acid sequences which are encoded by the nucleotide sequences above-described. Such amino acid sequences are capable of generating an immunogenic response against the novel AVS-1 astrovirus isolate. The present invention advantageously provides a fragment of a nucleotide sequence as disclosed above encoding an amino acid sequence which is capable of generating an immunogenic response against the novel AVS-1 astrovirus isolate. Such immunogenic peptides exhibit at least one antigenic site to which the immune response may be directed. The immunogenic response is against at last one antigenic site, such as for example the capsid protein of the AVS-1 astrovirus isolate.

The invention further provides a genetic construct carrying at least one nucleotide sequence as disclosed above or a portion thereof encoding an immunogenic peptide, under the control of promoter sequence which is operably linked to said nucleotide sequence, as well as a vector and host cells containing such genetic construct. Suitable vectors are well known in the art and include for example prokaryotic or eukaryotic plasmids, viruses, such as baculovirus, adenovirus, etc. . . . and yeast vectors. Host cells may be bacterial cells, insect cells, plant cells, yeast cells, etc. . . . . According to this aspect, there is provided a method of producing a peptide encoded by a nucleotide sequence as described above, comprising the step of: (i) contacting appropriate host cell with a vector as described above, and (ii) cultivating host cell under conditions suitable for the production of a polypeptide or a fragment thereof. Preferred host cells are bacterial cells such as *Escherichia coli*, or yeast cells such as *Pichia*. The invention thus provides an antigenic peptide obtainable by the above method. Antigenic peptide so obtained may be isolated and purified from the host cells culture in which it is expressed.

The invention thus also relates to polyclonal or monoclonal antibodies which specifically bind to such antigenic polypeptides, as well as a composition for vaccinating poultry comprising such antigenic polypeptides and/or a composition for treating poultry infections comprising such polyclonal or monoclonal antibodies.

In another embodiment, the present invention provides a vaccine which effectively affords protection in poultry against disease caused by avian astrovirus isolate of the new antigenic class, and a vaccine for immunization against runt stunting syndrome in poultry. In effect, vaccination may advantageously be used to control such disease, as vaccinated poultry are less susceptible to adverse effects caused by subsequent viral infections by the same infectious agent.

In general, appropriate antiserum raised against the live astrovirus isolate disclosed herein can be prepared by inoculating 3 to 4 weeks old chickens subcutaneously or intramuscularly with a live virus strain having an infectious titre between $10^2$-$10^9$ TC $ID_{50}$/animal; more preferably between $10^3$-$10^6$ TC $ID_{50}$/animal. Blood can be collected 3 to 4 weeks after infection, preferably 4 weeks after infection. Chickens may also be reinfected with the same live virus strain 3 to 4 weeks after the first infection with approximately the same dose as used in the first infection. Blood is collected between 2 and 4 weeks after the second infection.

Appropriate antiserum can also be raised against inactivated avian astrovirus strain isolate disclosed herein by inoculating 3 to 4 weeks old chickens subcutaneously or intramuscularly with the inactivated virus preparation. The infectious titre of the preparation before inactivation may be between $10'$-$10^{11}$ TC $ID_{50}$/animal; more preferably between $10^3$-$10^{10}$ TC $ID_{50}$/animal. Blood can be collected 3 to 4 weeks after inoculation, preferably 4 weeks after inoculation. Chickens may also be re-inoculated with the same inactivated virus preparation 3 to 6 weeks after the first inoculation. Blood is collected between 2 and 4 weeks after the second inoculation.

The present invention also provides a vaccine for use in the protection of poultry against disease conditions resulting from an avian astrovirus infection, such as MAS or runt stunting syndrome, comprising an avian astrovirus isolate according to the invention and a pharmaceutical acceptable carrier or diluent.

The astrovirus isolate according to the present invention can be incorporated into the vaccine as a live attenuated or inactivated virus. The property of the avian astrovirus isolate to induce MAS-associated disease conditions or runt runting syndrome conditions as described herein are significantly reduced or completely absent if the avian astrovirus is in a live attenuated or inactivated form.

Attenuation of the avian astrovirus isolate according to the invention can be achieved by methods well known in the art for this purpose, such as disclosed in Gouvea et al. (Virology 126:240-247, (1983)). Briefly, after the isolation of the virus from a target animal, a virus suspension is inoculated onto primary (avian) cell cultures such as chicken embryo liver cells (CEL), primary chicken embryo fibroblasts (CEFs) or Chicken kidney cells (CK) or mammalian cell lines such as the VERO cell line, BGM-70 cell line or avian cell line such as QT-35, QM-7 or LMH. If the isolate is not able to produce cytophatic effect (CPE), then the virus is passaged repeatedly (e.g. 3-10 times) until CPE is observed. As soon as CPE is visible, cells and cell culture fluids are collected, frozen and thawed, clarified by centrifugation and the supernatant containing the avian astrovirus isolate is aliquoted and stored at −20° C. This process may be repeated (e.g. 10-100 times) to further attenuate the virus.

In one embodiment, a vaccine according to the present invention can be prepared by conventional methods such as for example commonly used for the commercially available live- and inactivated astrovirus vaccines. For example, the preparation of veterinary vaccine compositions is described in "Vaccines for Veterinary Applications" (ed.: Peters, A. R. et al., Butterworth-Heinemann Ltd, 1993).

In one embodiment, the vaccine according to the present invention containing live attenuated virus can be prepared and marketed in the form of a (frozen) suspension or in a lyophilised form. The vaccine additionally may contain a pharmaceutically acceptable carrier or diluent customary used for such compositions. Carriers include stabilisers, preservatives and buffers. Suitable stabilisers are, for example, SPGA, carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

In another embodiment, the live vaccines according to the present invention may contain an adjuvant. Examples of suitable compounds and compositions with adjuvant activity are generally known in the art for the preparation of vaccines.

Although administration by injection, e.g., intramuscular, subcutaneous of the live vaccine according to the present invention is possible. The live vaccine is preferably administered by the inexpensive mass application techniques commonly used for avian astrovirus vaccination. These techniques include drinking water and spray vaccination. Alternative methods for administration of the live vaccine include in ovo, eye drop and beak dipping administration.

In another embodiment, the present invention provides a vaccine against MAS or runt runting syndrome and/or with avian nephritis, comprising the astrovirus isolate disclosed herein in an inactivated form. The major advantage of an inactivated vaccine is the elevated levels of protective antibodies of long duration that can be obtained. This property makes such an inactivated vaccine in particular suited for breeder vaccination.

The aim of inactivation of the viruses harvested after the propagation step is to eliminate reproduction of the viruses. In general, this can be achieved by chemical or physical means. Chemical inactivation can be effected by treating the viruses with, for example, enzymes, formaldehyde, beta-propiolactone, ethylene-imine or a derivative thereof. If necessary, the inactivating compound is neutralized afterwards. Material inactivated with formaldehyde can, for example, be neutralized with thiosulphate. Physical inactivation can preferably be carried out by subjecting the viruses to energy-rich radiation, such as UV light or γ-rays. If desired, after treatment the pH can be adjusted to a value of about 7.

A vaccine containing the inactivated avian astrovirus isolate AVS-1 disclosed herein can, for example, comprise one or more of the above-mentioned pharmaceutically acceptable carriers or diluents suited for this purpose. Preferably, an inactivated vaccine according to the present invention comprises one or more compounds with adjuvant activity. Suitable compounds or compositions for this purpose include aluminium hydroxide, -phosphate or -oxide, oil-in-water or water-in-oil emulsion based on, for example a mineral oil, such as Bayol F® or Marcol 52® or a vegetable oil such as vitamin E acetate, and saponins. In general, inactivated vaccines are usually administered parenterally, e.g., intramuscularly or subcutaneously.

The vaccine according to the present invention comprises an effective dosage of the astroviruses AVS-1 disclosed herein as the active component, i.e., an amount of immunizing avian astrovirus material that will induce immunity in the vaccinated birds or their progeny against challenge by a virulent virus. Immunity is defined herein as the induction of a significant higher level of protection in a population of birds after vaccination compared to an unvaccinated group. Typical doses and schedule for vaccination are generally known in the art, and take into account the age and/or weight and/or physical condition of the poultry.

The astrovirus vaccines according to the present invention may be used effectively in poultry such as chickens, as well as other poultry such as turkeys, guinea fowl goose, ostrich, peafowl, pigeon, swan, penguin, and quail. Chickens include broilers, reproduction stock and laying stock.

The present invention also provides combination vaccines comprising, in addition to the avian astrovirus of the present invention, one or more vaccine components of other pathogens infectious to poultry. In general, such other pathogens infectious to poultry are antigenically distinct from the astroviruses of the present invention. In one embodiment, the vaccine components in the combination vaccine are live attenuated or inactivated forms of the pathogens infectious to poultry. In another embodiment, the present invention provides a combination vaccine wherein all of the vaccine components are in an inactivated form.

In another embodiment, there is provided a vaccine for use in the protection of poultry against disease conditions resulting from an avian astrovirus infection, comprising the astrovirus isolate AVS-1 disclosed herein, and a pharmaceutical acceptable carrier. In general, the vaccine may comprise the avian astrovirus isolate AVS-1 in a live attenuated or inactivated form. The vaccine may further comprise an adjuvant. In another embodiment, the vaccine may further comprise one or more vaccine components against a second pathogen infectious to poultry. The combination vaccine comprises one or more virus in addition to the astrovirus novel serotype, such as a reovirus, an infectious bronchitis virus (IBV), Newcastle disease virus (NDV), infectious bursal disease virus (IBDV), fowl adenovirus (FAV), EDS virus and turkey rhinotracheitis virus (TRTV). Preferably, the combination vaccine comprises a reovirus as second pathogen.

In general, the vaccine may comprise astrovirus and the reovirus and in live attenuated or inactivated forms. The vaccine may further comprise an adjuvant.

The present invention also provides subunit vaccines comprising the astrovirus isolate AVS-1 of the present invention. Genes from the astrovirus isolate disclosed herein producing protective proteins against the disease are cloned into expression vectors or carriers generally known in the art. Expression of these protective proteins could then be produced as subunit vaccines according to standard procedures well-known in the art.

The present invention also provides recombinant vaccines comprising the astroviruses of the present invention. Genes from the astroviruses disclosed herein producing protective proteins against disease could be cloned into live or inactivated vectors or other carries generally known in the art for expression of these proteins as vaccines. In addition, these viruses themselves may be used as live attenuated vaccines (vectors) to carry genes producing protective proteins from other agents allowing for protection against the vector as well as the inserted gene.

The present invention also provides antiserum that is induced in an animal by the astrovirus and reoviruses isolates disclosed herein. The present invention also provides antibodies that bind to the astrovirus and reoviruses disclosed herein. In one embodiment, the antibodies are monoclonal antibodies. Immunization methods to provide monoclonal antibodies are well known in the art. These may include for example purification and inoculation to animal with astrovirus isolate AVS-1, and production of the monoclonal antibodies by hybridoma technique.

Antibody is intended to mean any molecule having a binding domain with the required specificity. An antibody may be natural or partly or wholly synthetically produced. The term also covers any polypeptide, protein or peptide having a binding domain homologous to an antibody binding domain. These can be derived from natural sources, or they may be partly or wholly synthetically produced. Examples of antibodies are the immunoglobulin isotypes and subclasses and fragments which comprise an antigen binding domain such as Fab, scFv, Fv, Fd and diabodies. In one embodiment, the antibodies are monoclonal antibodies, polyclonal antibodies, chimeric antibodies, or single chain antibodies, bispecific antibodies, synthetic antibodies, antibodies fragment such as Fab, F(ab)2, Fv, or scFv fragments, or chemically modified derivatives thereof.

Monoclonal antibodies can be prepared, for example, by the techniques which are well known to a skill person in the art. Such techniques involve the fusion of mouse myeloma cells to spleen cells derived from immunized mammals. Furthermore, antibodies, or fragments thereof, can be obtained by using methods which are described, for example, in Harlow and Lane, Antibodies, A Laboratory Manual, CSH Press, Cold Spring Harbor, 1988. Useful antibodies, or their corresponding immunoglobulin chain(s), can be further modified using conventional techniques known in the art, for example by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art (see, e.g., Sambrook, Molecular Cloning: A Laboratory Manual, Cold Spring Harbor Laboratory (1989) N.Y.).

The present invention also provides a method of protecting poultry against disease conditions, and particularly syndrome of MAS or nephritis resulting from an avian astrovirus and reovirus co-infection, comprising the step of administering the vaccine disclosed herein to the poultry. Examples of poultry include, but are not limited to, chickens, turkeys, guinea fowl, goose, ostrich, peafowl, pigeon, swan, penguin, and quail.

The present invention also provides antiserum that is induced in an animal by the astrovirus isolate disclosed herein. The present invention also provides antibodies that bind to the astrovirus isolate disclosed herein. In one embodiment, the antibodies are monoclonal antibodies.

The present invention also provides a method of protecting poultry against disease conditions resulting from an avian astrovirus infection, comprising the step of administering the vaccine disclosed herein to the poultry. Examples of poultry include, but are not limited to, chickens, turkeys, guinea fowl, goose, ostrich, peafowl, pigeon, swan, penguin, and quail.

Such vaccination includes any regimen, and may thus have curative, alleviation or prophylactic effects.

According to another embodiment, the present invention also provides with a method of detecting or a diagnostic assay for the detection of astrovirus isolate AVS-1 in poultry suspected from being infected with the virus, comprising the steps of: obtaining a sample from the poultry; contacting avian sample with a probe comprising a nucleotide sequence chosen among (i) a nucleotide sequence as set forth in SEQ ID NO: 1, (ii) a nucleotide sequence capable of hybridizing to SEQ ID NO: 1 under stringent conditions, (iii) a nucleotide sequence with at least 85%, 90%, 93%, 95%, 98%, 99% or 100% of identity with SEQ ID NO: 1, or a fragment from any one of the sequences (i), (ii) or (iii); and detecting binding between said probe and purified nucleotide from poultry samples. Detection of binding may be performed using a suitable marker associated with the probe such as a fluorescent marker, a radioisotope marker, or any other marker well known in the art.

The method of detecting and/or method of quantifying astrovirus isolate AVS-1 in poultry may comprise the steps of contacting a sample from poultry with an antibody which binds to the astrovirus isolate AVS-1 or the amino acid sequence encoded by nucleotide sequences as set forth in SEQ ID NO: 1, or by a sequence having at least 85%, 90%, 93%, 95%, or 97% homology with a nucleotide sequences as set forth in SEQ ID NO: 1, or by a sequence capable of hybridizing under stringent conditions with one or more nucleotide sequences selected from the group consisting of SEQ ID NO: 1, and measuring the amount of binding of the antibody to a component of the sample.

By way of example, the amount of novel reoviridae isolates in poultry may be measured using the ELISA assays. In practice, standards and samples to be tested are incubated in microtiter wells pre-coated with antibody that captures the reovirus. The standards and samples are diluted in a buffer containing detergent for 1 hour at room temperature prior to loading the microtiter wells. The captured reoviridae particles are then detected for example with biotinylated second antibody that binds to the reoviridae which is then detected for example by using a streptavidin-peroxidase conjugate and colored substrate. The concentration of the reoviridae particles is then determined using a standard curve prepared from known amounts of the reoviridae particles. ELISA techniques are well known to those of ordinary skill in the art.

Diagnostic kit or assay is preferably conducted with the appropriate forward and reverse primers by RT-PCR to amplify a selected target sequence of avian virus within the poultry sample. Suitable forward and reverse primers may comprise any suitable sequences from within the astrovirus isolate AVS-1. For example, such primers may comprise any nucleotide sequence from within the sequences chosen among (i) a nucleotide sequence as set forth in SEQ ID NO: 1, (ii) a nucleotide sequence capable of hybridizing to SEQ ID NO: 1 under stringent conditions, (iii) a nucleotide sequence with at least 85%, 90%, 93%, 95%, 98%, 99%, or 100% of identity with SEQ ID NO: 1, or a fragment from any one of the sequences (i), (ii) or (iii). The skilled person would easily design such primers using the sequence comparison to determine conserved regions of the sequence to which forward and reverse primers may be designed. Preferably, the assay provides quantitative information on the amount of astrovirus present in the sample. The primers are thus labeled fluorescently and the assay comprise a further step of determining if the primers have bound to the nucleotide sequence by determining the level of fluorescent emissions of the primers. Such fluorescent labels are well known in the art.

Suitable primers may have for example the following sequence 5'-ATT AGA ATG ATC TTG TGT ACA G-3' (SEQ ID NO: 2) and 5'-GAT AAG AGC CTA TCA TCA CC-3' (SEQ ID NO: 3).

Alternatively, the method of detecting the presence of avian astrovirus in poultry, comprises the steps of: obtaining a sample from the poultry, such as for example blood or feces; contacting the sample with antibodies which specifically bind to the astrovirus isolate AVS-1 disclosed herein or to at least one part of such astrovirus isolate; and detecting binding of the antibodies to the sample, wherein detected binding would indicate the presence of avian astrovirus isolate of the present invention in the poultry.

In general, the sample is prepared from intestine, liver, or feces of the poultry. Examples of poultry include, but are not limited to, chickens, turkeys, guinea fowl, goose, ostrich, peafowl, pigeon, swan, penguin, and quail. Astrovirus isolate AVS-1 or antibodies which are used to conduct such diagnosis assay may be immobilized on a solid support or substrate, thereby rendering easier the detection of any bound antibodies. The captured astrovirus isolate AVS-1 may be further detected by using antibodies conjugates which are well known in the art.

The present invention further provides a diagnostic kit comprising antibodies that bind to the astrovirus isolate AVS-1 disclosed herein, means for detecting antibodies, thereby allowing following the presence of avian astrovirus and the level of infection of poultry.

The present invention also relates to a novel propagation cell line which is derived from original LMH cell lines (ATCC accession number CRL 2117), which has been adapted as non-collagen dependent cell line and to grow on plastic plates. The novel propagation cell line LMH-KJ has been deposited with the American Type Culture Collection ("ATCC" 10801 University Boulevard, Manassas, Va. 20110-2209 USA) under Budapest Treaty on Jun. 26, 2008, and has accession number PTA-9299.

The present invention further relates to method of propagating novel isolated astrovirus serotype consisting in infecting the non-collagen dependent cell lines LMH-KJ, culturing the cells under same growing conditions as that of cells LMH ((ATCC accession number CRL 2117) with gentamicin, and harvesting astrovirus when cytophatic effect (CPE) is visible.

The age of the animals receiving a live or inactivated vaccine according to the invention is the same as that of the animals receiving the presently commercially available live- or inactivated avian virus vaccines. For example, broilers may be vaccinated directly from one-day-old onwards with the live attenuated vaccine according to the invention. Vaccination of parent stock, such as broiler breeders, can be done with a live attenuated or inactivated vaccine according to the invention or combinations of both. The advantages of this type of immunization program include the immediate protection of one-day-old progeny provided by maternally derived antibodies vertically transmitted to the young birds. A typical breeder vaccination program includes the vaccination of the breeders at 6-weeks of age with a live attenuated vaccine, followed by a vaccination between 14-18 weeks of age with an inactivated vaccine. Alternatively, the live vaccination may be followed by two vaccinations with inactivated vaccines on 10-12 weeks and 16-18 weeks of age.

Treatments according to the present invention are useful to modify immune system of an avian, thereby benefiting to said avian. The treatment may be prophylactic or curative. The treatment may be provided via any suitable route, and dose will depend upon nature of the antigen, route of administration and nature of the adjuvants.

The present invention finally provides a container comprising at least one dose of the vaccine as described herein, and a kit comprising such container with an instruction manual, including information for the administration of at least one dose of the vaccine to poultry for lessening the severity of the MAS or nephritis syndromes.

The invention being generally described, will be more readily understood by reference to the following examples which are included merely for purposes of illustration of certain aspects and embodiments of the present invention, and are not intended to limit the invention.

EXAMPLES

Example 1

Isolation of Astroviruses

The novel astrovirus serotype disclosed herein has been isolated from several infected chickens, West Virginia, USA. The astroviruses were cultivated in an adapted hepatocellular carcinoma cell line (CH-SAH, which is alternatively called the LMH cell line). The original LMH cell line was obtained from the American Type Culture Collection (ATCC), accession number ATCC CRL 2117 and has been adapted to be non-collagen dependent.

Example 2

Figure 1:
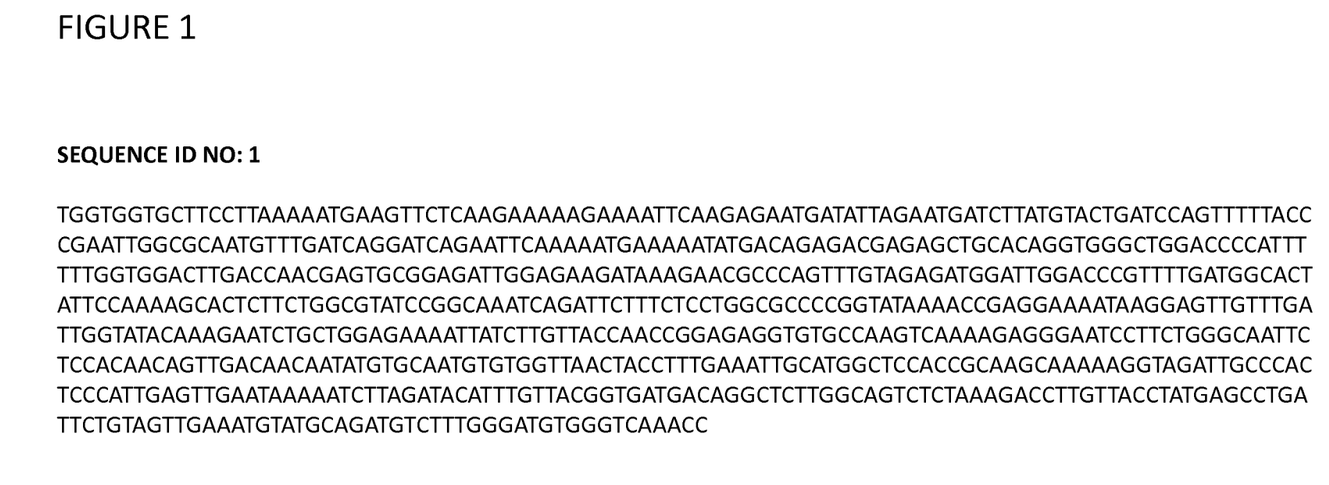
FIG. 1: shows part of the nucleotide sequence (SEQ ID NO: 1) corresponding to the polymerase gene of the AVS-1 astrovirus isolate.
Figure 2A:
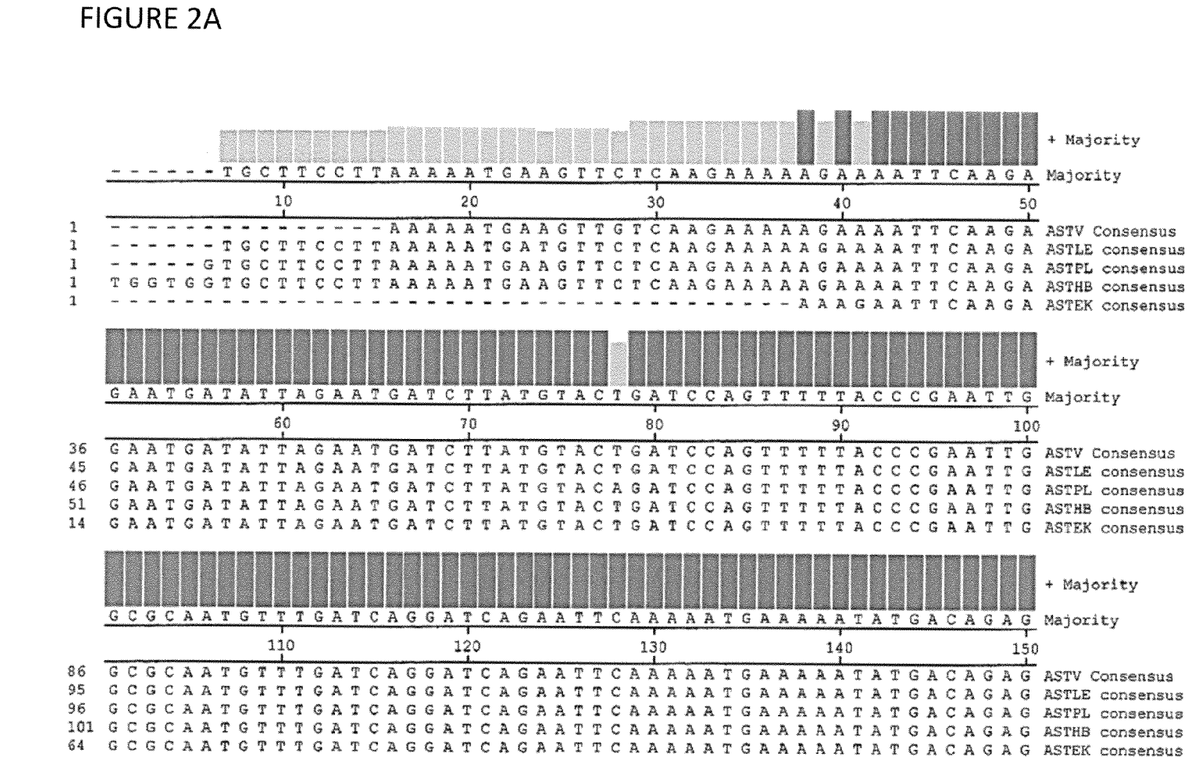
Figure 2B:
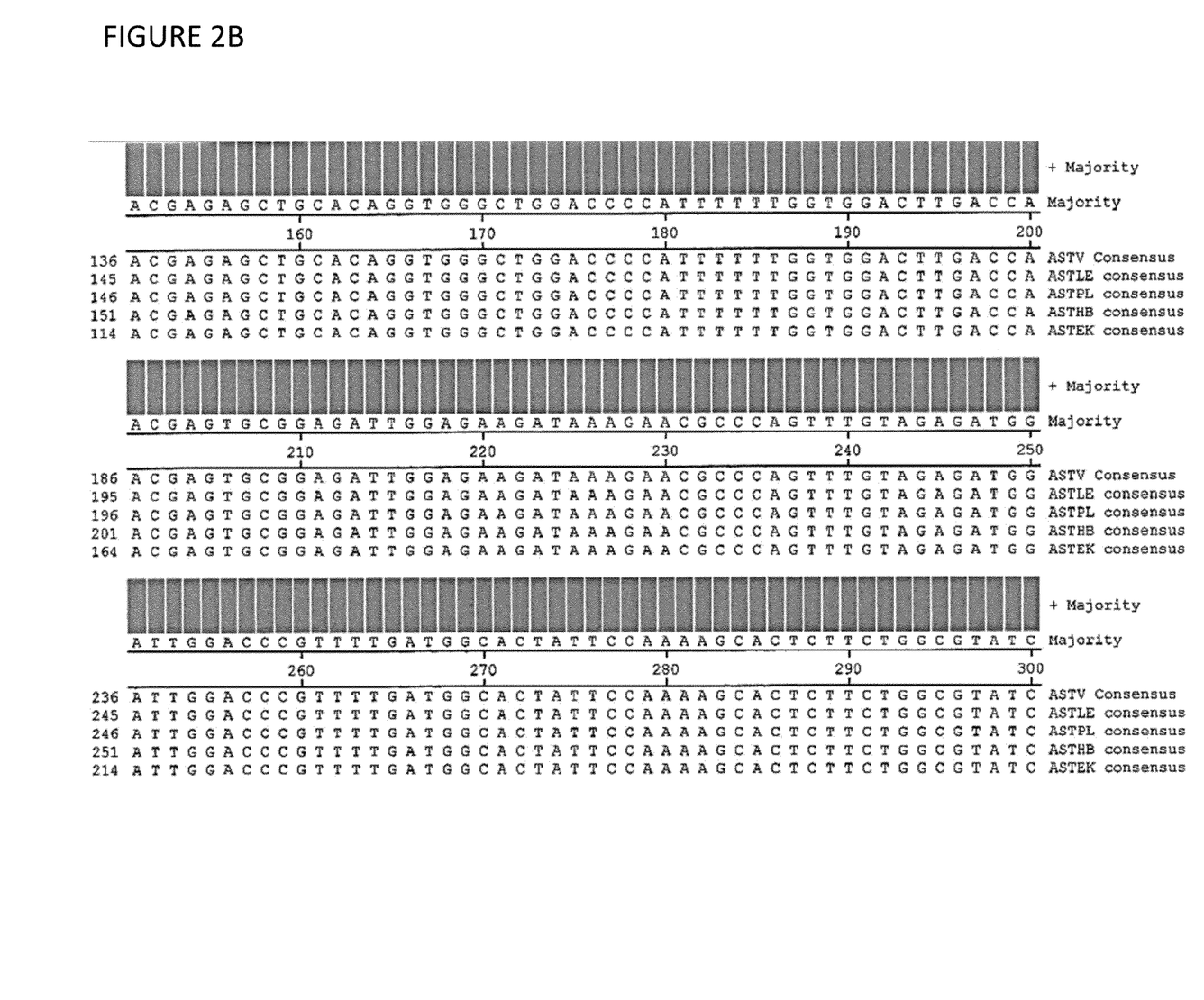
Figure 2C:
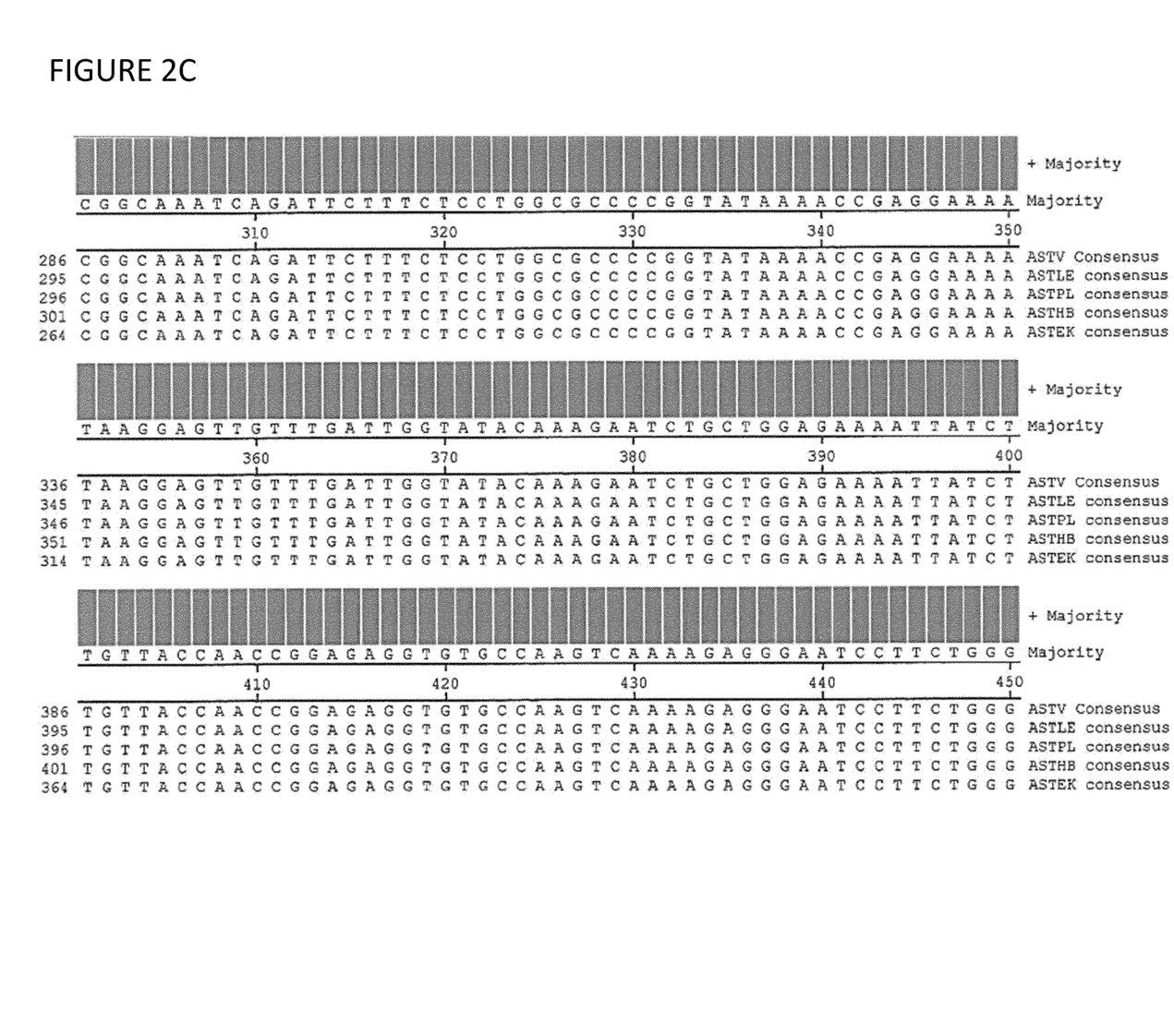
Figure 2D:
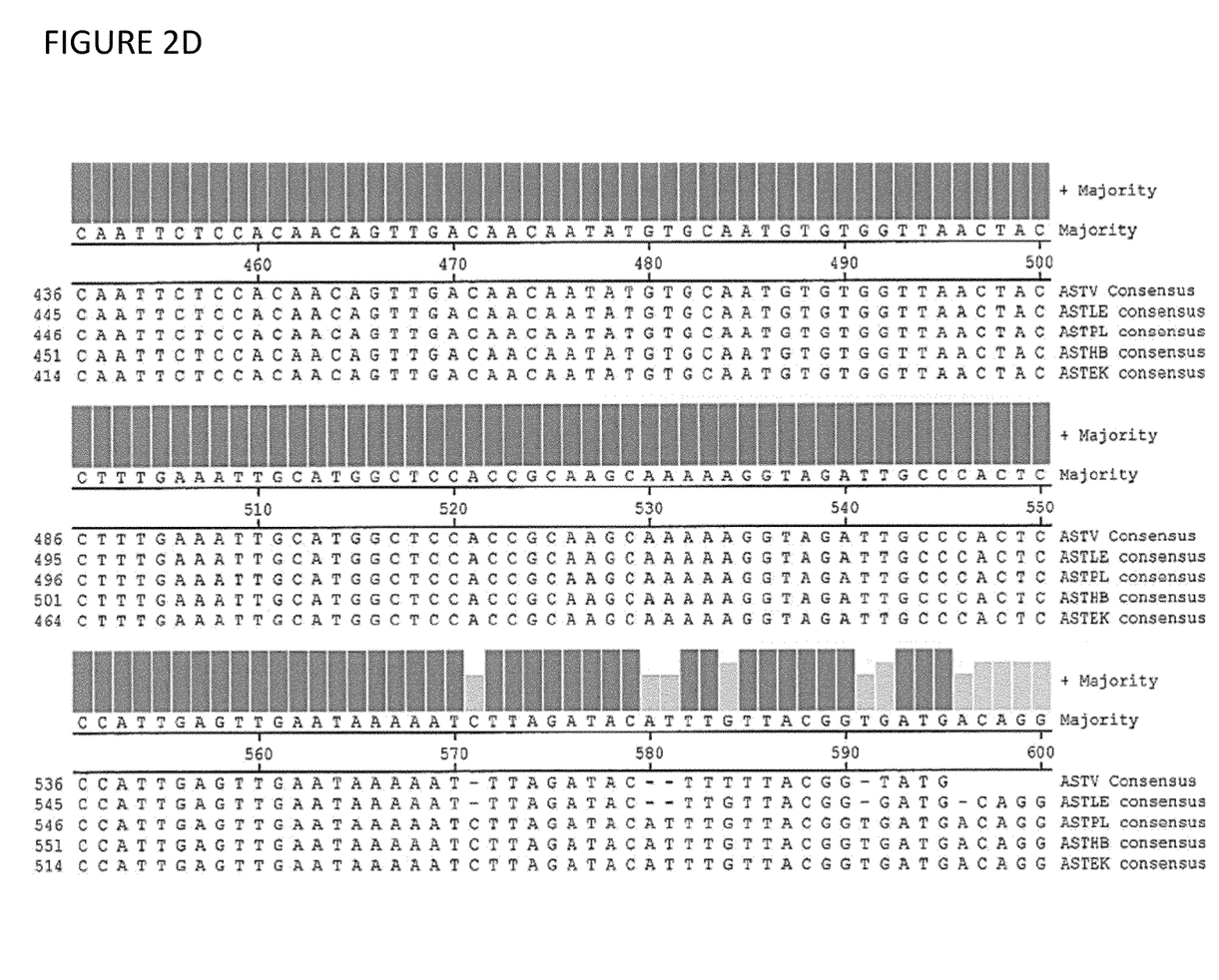
Figure 2E:
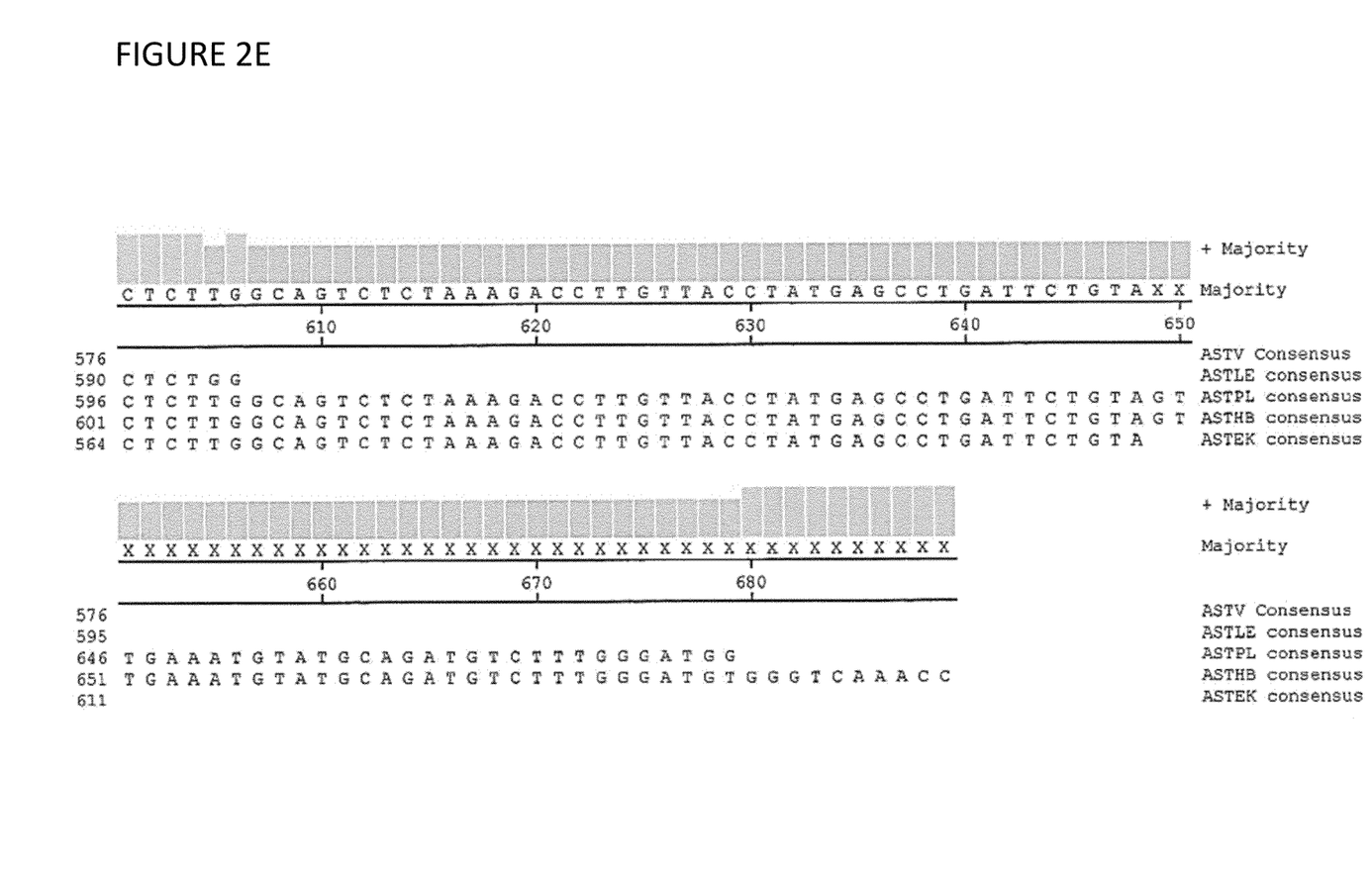
Figure 3:
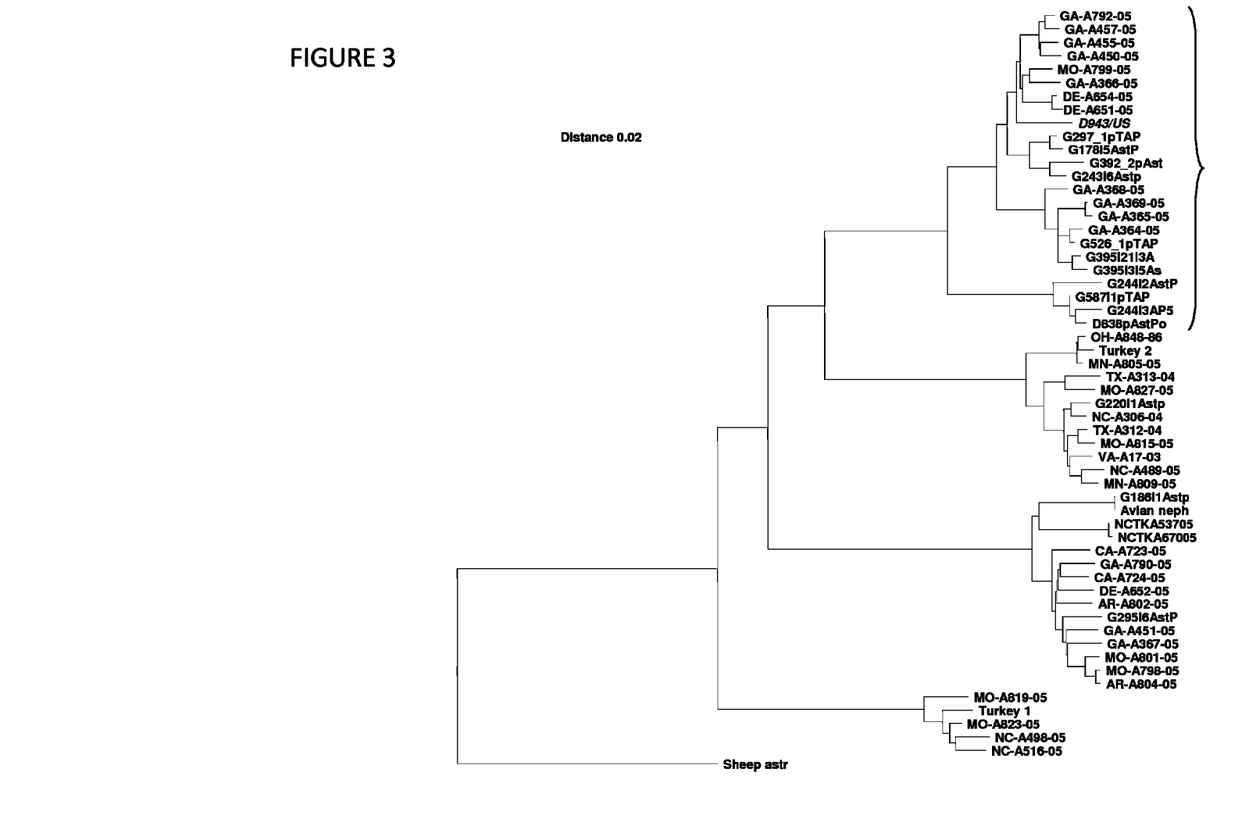
FIG. 3: displays the phylogenic tree of various avian astrovirus sequences.
Figure 4:
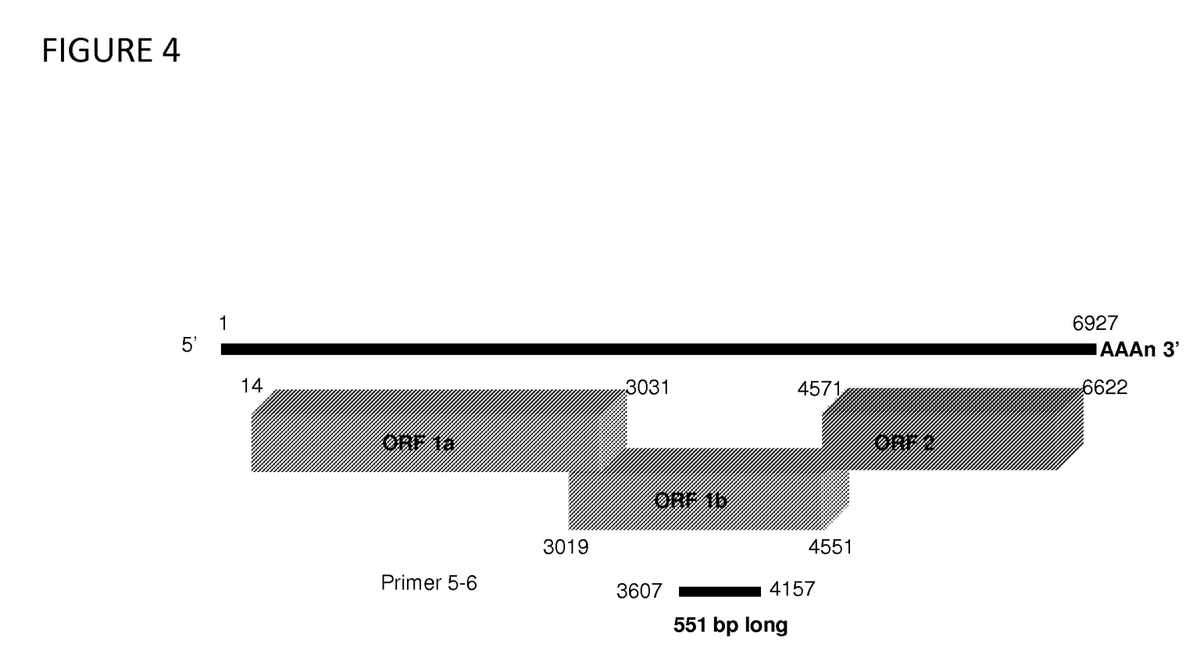
FIG. 4: shows the genome structure of the isolated avian astrovirus AVS-1 and location of the primer used for the molecular characterization of the AVS-1 isolate.

Amplification of Partial Sequence of Astrovirus Isolate AVS-1 and Comparison to Other Isolates from Similar Clinical Cases The viral RNA was extracted by TRI reagent (Sigma) according to the manufacturer instructions. Reverse transcription was performed for 60 min at 37° C. in 25 µl standard reaction mixes containing MMLV-reverse transcriptase (Promega) and random hexamer. The primers covered the most conserved region of the polymerase gene (ORF1b) from 3544 to 4235 nt as displayed in FIG. 4. The external primers amplified a 691 bp PCR product (forward AstPol1: 5'-CCA CTT TGG TGG TGC TT-3' (SEQ ID NO: 2), reverse AstPol2: 5'-GGT TTG ACC CAC ATC CCA A-3' (SEQ ID NO: 3)). The PCR reaction was carried out on 5 µl of samples from cDNA as template in the presence of 75 µM of each dNTPs, 0.2 µM of each primers, 2U Taq polymerase (Fermentas) and 2.5 mM $MgCl_2$. The PCR program was: initial denaturation at 94° C. for 1 min, 35 cycles at 94° C. for 30 sec, 50° C. for 30 sec, 72° C. for 1 min and final extension at 72° C. for 5 min.

Using the primers and procedures described above, DNA was amplified from astroviruses isolated from similar clinical cases in Delaware (designated ASTV, ASTLE, ASTPL, ASTEK). Using the ClustalW multiple sequence alignment program, the nucleotide sequence alignment revealed 99.3-99.7% similarity to the AVS-1 isolate.

Example 3

Efficacy of Inactivated Astrovirus Vaccine

Progeny chicks from breeder hens that were vaccinated four times with an inactivated astrovirus vaccine were challenged with astrovirus to evaluate the efficacy of the vaccine. The vaccine was made by inactivating AVS-1 with 0.2% formalin (final concentration) and adjuvanted with an oil based adjuvant. Specific pathogen free (SPF) chickens were vaccinated subcutaneously two times with 0.5 ml of the inactivated astrovirus vaccine at 2 and 21 weeks of age. The chickens were bled at 2, 4 and 8 weeks post the $1^{st}$ vaccination and at 3 weeks post the $2^{nd}$ vaccination. Collected sera were used for the VN test using AVS-1 antigen to monitor development of neutralizing antibodies against astrovirus. Progeny chickens from the vaccinated chickens were also bled at hatch to monitor maternally transferred antibodies in the progeny. Eggs were collected twice, between 3 and 4 weeks after the $2^{nd}$ vaccination and between 4 and 5 weeks after the $2^{nd}$ vaccination.

The hens vaccinated with the astrovirus vaccine developed significantly higher VN titers (891) against astrovirus by 4 weeks post vaccination (Table 1). The elevated antibody level was sustained at least until 8 weeks post vaccination. Unvaccinated controls did not show any VN titers. After hens were boosted at 21 weeks old, the VN titers further increased to approximately 1900. Progeny chicks hatched from eggs collected after boost also possessed higher VN titers against astrovirus (Table 2), suggesting that neutralizing antibodies in the hens were effectively transferred to the progeny chicks.

Progeny chicks from eggs that were collected 3 to 4 weeks post $2^{nd}$ vaccination of the hens, were hatched. At day of age, these progeny chicks were challenged with AVS-1 and subsequently necropsied. In treatment group 1, containing progeny from vaccinated hens, 2 out of 14 (14%) chickens were susceptible to virulent astrovirus challenge (Table 3). In treatment group 2, containing non-vaccinated, SPF chickens that were challenged with astrovirus, 9 out of 15 (60%) chickens were susceptible to virulent astrovirus challenge. In other words, 12 out of 14 chickens (86%) of the progeny from vaccinated hens were protected against challenge while 40% of the non-vaccinated, astrovirus challenged positive control group was protected.

TABLE 1

Virus neutralization geometric mean titers against astrovirus in hens

| Group # | Treatment Group | 2 weeks post $1^{st}$ vaccination | 4 weeks post $1^{st}$ vaccination | 8 weeks post $1^{st}$ vaccination | 3 weeks post $2^{nd}$ vaccination |
|---|---|---|---|---|---|
| 1 | Astrovirus vaccine | 12 | 891 | 845 | 1855 |
| 2 | Negative controls | 2 | 2 | 2 | Not done |

TABLE 2

Virus neutralization geometric mean titers against astrovirus in progeny chicks

| | | Egg collection period | |
| --- | --- | --- | --- |
| Group # | Treatment Group | 3 to 4 weeks post 2$^{nd}$ vaccination | 4 to 5 weeks post 2$^{nd}$ vaccination |
| 1 | Astrovirus vaccine | 104 | 128 |

TABLE 3

Efficacy of progeny chicks 3 to 4 weeks post 2$^{nd}$ vaccination against virulent Astrovirus challenge

| Group # | Treatment Group | # positive/total # of chicks following virulent astrovirus challenge (% susceptible) |
| --- | --- | --- |
| 1 | Progeny from Astrovirus Vaccinated Hens | 2/14 (14%) |
| 2 | Non-vaccinated, challenged controls | 9/15 (60%) |

What is claimed is:

1. An isolated astrovirus serotype, designated AVS-1, comprising SEQ ID NO: 1, a sample of which is deposited at the ATCC under accession number PTA-9298.

2. A vaccine for protecting poultry against a disease condition resulting from an avian astrovirus infection, comprising, an inactivated form of the astrovirus isolate, designated AVS-1, comprising SEQ ID NO: 1, a sample of which is deposited at the ATCC under accession number PTA-9298, and, optionally, an adjuvant.

3. The vaccine of claim 2, wherein the vaccine further comprises one or more vaccine components against a second pathogen infectious to poultry.

4. The vaccine of claim 2, wherein the disease condition is runt stunting syndrome or avian malabsorption syndrome (MAS).

5. The vaccine of claim 2, wherein the poultry is a chicken, turkey, guinea fowl, goose, ostrich, peafowl, pigeon, swan, penguin, or quail.

6. A method of protecting or vaccinating poultry against disease conditions resulting from an avian astrovirus infection comprising administering to the poultry an immunogenically effective amount of the vaccine of claim 2.

7. The method of claim 6, wherein the poultry is a chicken, turkey, guinea fowl, goose, ostrich, peafowl, pigeon, swan, penguin, or quail.

8. The method of claim 6, wherein the disease is runt stunting syndrome or avian malabsorption syndrome (MAS).

9. A method of propagating astrovirus, comprising infecting an adapted hepatocellular carcinoma (LMH) cell line with the astrovirus according to claim 1, culturing the cells under growing conditions and harvesting astrovirus when said cell line exhibits visible cytopathic effects.

10. A cell line which is deposited at the ATCC under accession number PTA-9299.

11. The vaccine of claim 3, wherein said second pathogen is a reovirus.

12. The vaccine of claim 4, wherein the disease condition is an acute disease form of runt stunting syndrome or MAS.

13. The vaccine of claim 2, wherein said vaccine comprises an adjuvant and an inactivated form of the astrovirus isolate, designated AVS-1, comprising SEQ ID NO: 1, a sample of which is deposited at the ATCC under accession number PTA-9298.

14. The method of claim 9, wherein said LMH cell line is a non-collagen dependent cell line designated LMH-KJ and is deposited at the ATCC under accession number PTA-9299.

15. A cell culture comprising culture medium and a cell line infected with the astrovirus according to claim 1.

16. The cell culture according to claim 15, wherein said cell line is an avian cell line.

* * * * *

UNITED STATES PATENT AND TRADEMARK OFFICE
CERTIFICATE OF CORRECTION

PATENT NO. : 8,790,657 B2  
APPLICATION NO. : 13/000477  
DATED : July 29, 2014  
INVENTOR(S) : Kristi Mae Dorsey et al.

Page 1 of 1

It is certified that error appears in the above-identified patent and that said Letters Patent is hereby corrected as shown below:

In the Specification

Column 3,  
Line 63, "("ATCC" University" should read --("ATCC" 10801 University--.

Column 5,  
Line 48, "10'-$10^{11}$" should read --$10^7$-$10^{11}$--.  
Line 49, "$10^3$-$10^{10}$" should read --$10^8$-$10^{10}$--.

Column 11,  
Line 60, "Tag polymerase" should read --*Taq* polymerase--.

Signed and Sealed this  
Twenty-first Day of April, 2015

Michelle K. Lee  
*Director of the United States Patent and Trademark Office*

SEQUENCE LISTING

<160> NUMBER OF SEQ ID NOS: 7

<210> SEQ ID NO 1
<211> LENGTH: 689
<212> TYPE: DNA
<213> ORGANISM: Astrovirus

<400> SEQUENCE: 1

```
tggtggtgct tccttaaaaa tgaagttctc aagaaaaaga aaattcaaga gaatgatatt      60
agaatgatct tatgtactga tccagttttt acccgaattg gcgcaatgtt tgatcaggat     120
cagaattcaa aaatgaaaaa tatgacagag acgagagctc cacaggtggg ctggaccccca    180
tttttttggtg gacttgacca acgagtgcgg agattggaga agataaagaa cgcccagttt    240
gtagagatgg attggacccg ttttgatggc actattccaa aagcactctt ctggcgtatc     300
cggcaaatca gattctttct cctggcgccc cggtataaaa ccgaggaaaa taaggagttg     360
tttgattggt atacaaagaa tctgctggag aaaattatct tgttaccaac cggagaggtg     420
tgccaagtca aaagagggaa tccttctggg caattctcca caacagttga caacaatatg     480
tgcaatgtgt ggttaactac ctttgaaatt gcatggctcc accgcaagca aaaaggtaga     540
ttgcccactc ccattgagtt gaataaaaat cttagataca tttgttacgg tgatgacagg     600
ctcttggcag tctctaaaga ccttgttacc tatgagcctg attctgtagt tgaaatgtat     660
gcagatgtct ttgggatgtg ggtcaaacc                                       689
```

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2

```
attagaatga tcttgtgtac ag                                              22
```

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3

```
gataagagcc tatcatcacc                                                 20
```

<210> SEQ ID NO 4
<211> LENGTH: 580
<212> TYPE: DNA

<213> ORGANISM: Astrovirus

<400> SEQUENCE: 4

```
aaaaatgaag ttgtcaagaa aagaaaatt caagagaatg atattagaat gatcttatgt      60
actgatccag tttttacccg aattggcgca atgtttgatc aggatcagaa ttcaaaaatg    120
aaaaatatga cagagacgag agctgcacag gtgggctgga ccccatttt tggtggactt    180
gaccaacgag tgcggagatt ggagaagata agaacgccc agtttgtaga gatggattgg    240
acccgttttg atggcactat ccaaaagca ctcttctggc gtatccggca atcagattc    300
tttctcctgg cgccccggta taaaccgag gaaaataagg agttgtttga ttggtataca    360
aagaatctgc tggagaaaat tatcttgtta ccaaccggag aggtgtgcca agtcaaaaga    420
gggaatcctt ctgggcaatt ctccacaaca gttgacaaca atatgtgcaa tgtgtggtta    480
actacctttg aaattgcatg gctccaccgc aagcaagcaa aaggtagat tgcccactcc    540
cattgagttg aataaaaatt tagatacttt ttacggtatg                          580
```

<210> SEQ ID NO 5
<211> LENGTH: 599
<212> TYPE: DNA
<213> ORGANISM: Astrovirus

<400> SEQUENCE: 5

```
tgcttcctta aaatgatgt tctcaagaaa agaaaattc aagagaatga tattagaatg      60
atcttatgta ctgatccagt ttttacccga attggcgcaa tgtttgatca ggatcagaat    120
tcaaaaatga aaaatatgac agagacgaga gctgcacagg tgggctggac ccatttttt    180
ggtggacttg accaacgagt gcggagattg gagaagataa agaacgccca gtttgtagag    240
atggattgga cccgttttga tggcactatt ccaaaagcac tcttctggcg tatccggcaa    300
atcagattct ttctcctggc gccccggtat aaaccgagg aaaataagga gttgtttgat    360
tggtatacaa agaatctgct ggagaaaatt atcttgttac caaccggaga ggtgtgccaa    420
gtcaaaagag ggaatcctc tgggcaattc tccacaacag ttgacaacaa tatgtgcaat    480
gtgtggttaa ctacctttga aattgcatgg ctccaccgca agcaagcaaa aggtagatt    540
gcccactccc attgagttga ataaaaattt agatacttgt tacgggatgc aggctctgg    599
```

<210> SEQ ID NO 6
<211> LENGTH: 678
<212> TYPE: DNA
<213> ORGANISM: Astrovirus

<400> SEQUENCE: 6

```
gtgcttcctt aaaatgaag ttctcaagaa aagaaaatt caagagaatg atattagaat      60
gatcttatgt acagatccag tttttacccg aattggcgca atgtttgatc aggatcagaa    120
ttcaaaaatg aaaaatatga cagagacgag agctgcacag gtgggctgga ccccatttt    180
tggtggactt gaccaacgag tgcggagatt ggagaagata agaacgccc agtttgtaga    240
gatggattgg acccgttttg atggcactat ccaaaagca ctcttctggc gtatccggca    300
aatcagattc tttctcctgg cgccccggta taaaccgag gaaaataagg agttgtttga    360
ttggtataca aagaatctgc tggagaaaat tatcttgtta ccaaccggag aggtgtgcca    420
agtcaaaaga gggaatcctt ctgggcaatt ctccacaaca gttgacaaca atatgtgcaa    480
tgtgtggtta actacctttg aaattgcatg gctccaccgc aagcaagcaa aaggtagat    540
tgcccactcc cattgagttg aataaaaatc ttagatacat ttgttacggt gatgacaggc    600
```

-continued

```
tcttggcagt ctctaaagac cttgttacct atgagcctga ttctgtagtt gaaatgtatg      660
cagatgtctt tgggatgg                                                   678

<210> SEQ ID NO 7
<211> LENGTH: 615
<212> TYPE: DNA
<213> ORGANISM: Astrovirus

<400> SEQUENCE: 7
aaagaattca agagaatgat attagaatga tcttatgtac tgatccagtt tttacccgaa       60
ttggcgcaat gtttgatcag gatcagaatt caaaaatgaa aaatatgaca gagacgagag      120
ctgcacaggt gggctggacc ccatttttg gtggacttga ccaacgagtg cggagattgg       180
agaagataaa gaacgcccag tttgtagaga tggattggac ccgttttgat ggcactattc      240
caaaagcact cttctggcgt atccggcaaa tcagattctt tctcctggcg ccccggtata      300
aaaccgagga aaataaggag ttgtttgatt ggtatacaaa gaatctgctg gagaaaatta      360
tcttgttacc aaccggagag gtgtgccaag tcaaagagg gaatccttct gggcaattct      420
ccacaacagt tgacaacaat atgtgcaatg tgtggttaac tacctttgaa attgcatggc      480
tccaccgcaa gcaagcaaaa aggtagattg cccactccca ttgagttgaa taaaaatctt      540
agatacattt gttacggtga tgacaggctc ttggcagtct ctaaagacct tgttacctat      600
gagcctgatt ctgta                                                      615
```